(12) United States Patent
Kudo

(10) Patent No.: US 10,603,097 B2
(45) Date of Patent: Mar. 31, 2020

(54) TREATMENT ENERGY APPLICATION STRUCTURE AND MEDICAL TREATMENT DEVICE

(71) Applicant: Olympus Corporation, Hachioji-shi, Tokyo (JP)

(72) Inventor: Koichi Kudo, Hachioji (JP)

(73) Assignee: Olympus Corporation, Tokyo (JP)

( * ) Notice: Subject to any disclaimer, the term of this patent is extended or adjusted under 35 U.S.C. 154(b) by 371 days.

(21) Appl. No.: 15/673,722

(22) Filed: Aug. 10, 2017

(65) Prior Publication Data

US 2017/0367750 A1     Dec. 28, 2017

Related U.S. Application Data

(63) Continuation of application No. PCT/JP2015/054875, filed on Feb. 20, 2015.

(51) Int. Cl.
*A61B 18/04* (2006.01)
*A61B 18/08* (2006.01)
(Continued)

(52) U.S. Cl.
CPC ............ *A61B 18/085* (2013.01); *A61B 18/04* (2013.01); *H05K 1/028* (2013.01); *H05K 1/0212* (2013.01);
(Continued)

(58) Field of Classification Search
CPC ... A61B 18/04; A61B 18/085; A61B 18/1445; A61B 2017/00017; A61B 2017/00973;
(Continued)

(56) References Cited

U.S. PATENT DOCUMENTS 6,053,914 A * 4/2000 Eggers ............... A61B 18/1445
606/174
2008/0200955 A1 8/2008 Tepic
(Continued)

FOREIGN PATENT DOCUMENTS

JP     2007-536986      12/2007
JP     2008-531078       8/2008
(Continued)

OTHER PUBLICATIONS

Office action dated Nov. 5, 2018 for the corresponding Chinese application CN2015-80062736.4.
(Continued)

*Primary Examiner* — Daniel W Fowler
(74) *Attorney, Agent, or Firm* — Matthew M. Eslami

(57) ABSTRACT

A treatment energy application structure includes a flexible substrate having an electric resistance pattern and a lead wire connection portion. A heat transfer plate faces the flexible substrate and transfers heat to the body tissue. An insulating adhesive sheet is interposed between the flexible substrate and the heat transfer plate. The insulating adhesive sheet comprises a first area to cover an entire surface of the electric resistance pattern and the heat transfer plate and a second area protruding from the heat transfer plate to cover a part of the lead wire connection portion. The heat transfer plate has a chamfered corner facing the insulating adhesive sheet. An adhesive may adhere the second area to at least one of the heat transfer plate and the substrate. The insulating adhesive sheet may adhere the substrate to both the heat transfer plate and the bridge portion of a cover.

12 Claims, 6 Drawing Sheets

(51) Int. Cl.
*H05K 1/02* (2006.01)
*A61B 17/00* (2006.01)
*A61B 18/00* (2006.01)

(52) U.S. Cl.
CPC .............. *A61B 2017/00951* (2013.01); *A61B 2018/00083* (2013.01); *A61B 2018/00095* (2013.01)

(58) Field of Classification Search
CPC ........... A61B 2018/00095; A61B 2018/00619; A61B 2018/00994
See application file for complete search history.

(56) References Cited

U.S. PATENT DOCUMENTS

| | | | | |
|---|---|---|---|---|
| 2009/0112200 A1* | 4/2009 | Eggers | ............... | A61B 17/3211 606/29 |
| 2011/0077630 A1* | 3/2011 | Tanaka | ................ | A61B 18/085 606/29 |
| 2013/0253508 A1* | 9/2013 | Ide | ...................... | A61B 18/085 606/41 |
| 2015/0289922 A1 | 10/2015 | Yasunaga | | |
| 2017/0215938 A1 | 8/2017 | Yasunaga | | |

FOREIGN PATENT DOCUMENTS

| | | |
|---|---|---|
| JP | 2014-124491 | 7/2014 |
| WO | WO 2005-115545 | 12/2005 |
| WO | WO 2006-089695 | 8/2006 |
| WO | WO 2014/103442 A1 | 7/2014 |

OTHER PUBLICATIONS

English Translation of International Search Report and Written Opinion dated Apr. 21, 2015 issued in PCT/JP2015/054875, 6 pages.

\* cited by examiner

TREATMENT ENERGY APPLICATION STRUCTURE AND MEDICAL TREATMENT DEVICE

CROSS-REFERENCE TO RELATED APPLICATION(S)

This application is a continuation application of PCT Application No. PCT/JP2015/054875 filed Feb. 20, 2015, which is hereby incorporated by reference in its entirety.

TECHNICAL FIELD

The present invention relates to a treatment energy application structure and a medical treatment device.

BACKGROUND

In recent years, there is known medical treatment devices having a treatment energy application structure for applying energy to a body tissue to perform a treatment (sealing or anastomosis) on a body tissue In a traditional method treatment energy application structure comprises a flexible substrate, a heat transfer plate, and an adhesive sheet.

The flexible substrate is a portion that serves as a sheet heater. The flexible substrate has, on one surface thereof, an electric resistance pattern for generating heat by power supply, and a lead wire connection portion which is configured to be electrically connected to the electric resistance pattern and to which a lead wire is connected.

The heat transfer plate is formed of a conducting material such as copper. The heat transfer plate faces one surface (the electric resistance pattern) of the flexible substrate and is configured to contact a body tissue to transfer a heat generated from the electric resistance pattern to the body tissue (to apply heat energy to the body tissue).

The adhesive sheet has good thermal conductivity and electrical insulation properties. The adhesive sheet is interposed between the flexible substrate and the heat transfer plate and allows them to adhere to each other.

Here, the adhesive sheet comprises a first area in which the adhesive sheet covers the entirety of the heat transfer plate when viewed from the thickness direction of the adhesive sheet and a second area in which the adhesive sheet protrudes from the heat transfer plate and covers a part of the lead wire connection portion. That is, the adhesive sheet has a function of thermally connecting the heat transfer plate and the electric resistance pattern to each other and preventing short-circuiting of the heat transfer plate and the electric resistance pattern by the use of the first area and has a function of preventing short-circuiting of the heat transfer plate and the lead wire connection portion by the second area.

SUMMARY

The present invention provides a treatment energy application structure. In one aspect the structure includes a flexible substrate. The flexible substrate has on one surface thereof, an electric resistance pattern and a lead wire connection portion. The electric resistance pattern is configured to generate heat by power supply. The lead wire connection portion is configured to be electrically connected to the electric resistance pattern and connected to a lead wire. A heat transfer plate faces the one surface of the flexible substrate. The heat transfer plate is configured to contact a body tissue to transfer the heat from the electric resistance pattern to the body tissue. An insulating adhesive sheet is interposed between the flexible substrate and the heat transfer plate to allow the flexible substrate and the heat transfer plate to adhere to each other. The insulating adhesive sheet comprises a first area to cover at least an entire surface of the electric resistance pattern and the heat transfer plate and a second area protruding from the heat transfer plate to cover a part of the lead wire connection portion. The heat transfer plate has a corner facing the insulating adhesive sheet. The corner is subject to a chamfer.

In another aspect a treatment energy application structure includes a flexible substrate having, on one surface thereof, an electric resistance pattern and a lead wire connection portion. The electric resistance pattern is configured to generate heat by power supply. The lead wire connection portion is configured to be electrically connected to the electric resistance pattern and connected to a lead wire. A heat transfer plate faces the one surface of the flexible substrate. An insulating adhesive sheet is interposed between the flexible substrate and the heat transfer plate to adhere to each other. The insulating adhesive sheet comprises a first area to cover the entirety of the electric resistance pattern and a second area protruding from the heat transfer plate to cover a part of the lead wire connection portion. The heat transfer plate has a corner facing the insulating adhesive sheet. The corner is subject to a chamfer.

In another aspect a treatment energy application structure includes a substrate having, on one surface thereof, an electric resistance pattern and a lead wire connection portion. The electric resistance pattern is configured to generate heat by power supply. The lead wire connection portion is configured to be electrically connected to the electric resistance pattern and connected to a lead wire. A heat transfer plate faces the one surface of the flexible substrate. An insulating adhesive sheet is interposed between the substrate and the heat transfer plate to adhere to each other. The insulating adhesive sheet comprises a first area to cover the entirety of the heat transfer plate and a second area protruding from the heat transfer plate to cover a part less than the entirety of the lead wire connection portion. An adhesive adheres the second area to at least one of the heat transfer plate and the substrate.

In another aspect a treatment energy application structure includes a substrate having, on one surface thereof, an electric resistance pattern and a lead wire connection portion. The electric resistance pattern is configured to generate heat by power supply. The lead wire connection portion is configured to be electrically connected to the electric resistance pattern and connected to a lead wire. A heat transfer plate faces the one surface of the substrate. A cover comprises a bridge portion facing the one surface of the substrate. An insulating adhesive sheet is interposed between the substrate and both the heat transfer plate and the bridge portion to allow the substrate to adhere to both the heat transfer plate and the bridge portion. The insulating adhesive sheet comprises a first area to cover the entirety of the heat transfer plate and a second area protruding from the heat transfer plate to cover a part of the lead wire connection portion. The bridge portion faces the substrate through the second area.

DESCRIPTION OF EMBODIMENTS

Detailed Description

As the above-described adhesive sheet, adhesive sheets have been widely used which effect an adhesion function by a pressure applied thereto.

That is, when the treatment energy application structure is assembled, the adhesive sheet is pressed in such a manner that a pressure is applied to the flexible substrate and the heat transfer plate while the adhesive sheet is interposed between the flexible substrate and the heat transfer plate. Accordingly, the adhesive sheet effects an adhesion function and allows the flexible substrate and the heat transfer plate to adhere to each other.

Here, when a pressure is applied as described above while the heat transfer plate has an edge, a pressure is intensively applied from the edge portion to a boundary portion between the first area and the second area of the adhesive sheet. As a result, a load may be applied to the adhesive sheet. The same situation may occur when the medical treatment device is used, that is, when the treatment energy application structure contacts a body tissue.

The invention has been made in view of the foregoing, and an object of the invention is to provide a treatment energy application structure and a medical treatment device capable of reducing a load on an adhesive sheet.

According to the treatment energy application structure and the medical treatment device of the present invention, it is possible to reduce a load on the adhesive sheet.

Hereinafter, features for carrying out the invention (hereinafter referred to as embodiment(s)) will be described with reference to the drawings. The embodiments to be described below do not limit the invention. The same reference signs are used to designate the same elements throughout the drawings.

Figure 1:
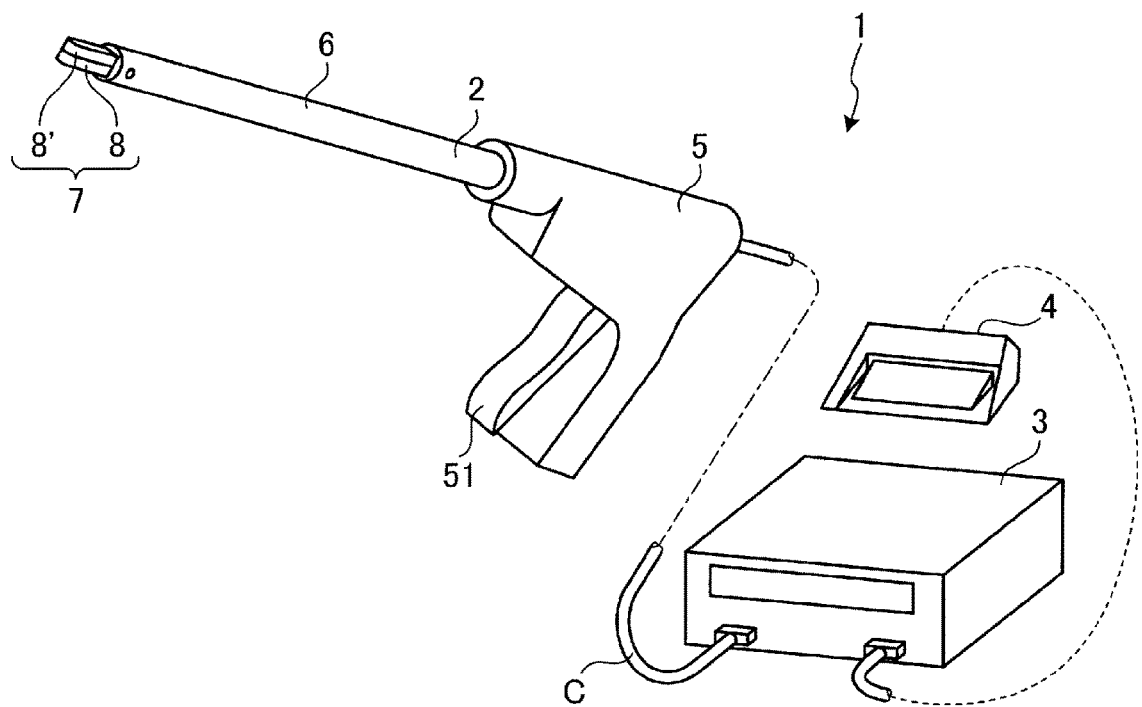
FIG. 1 is a diagram schematically illustrating a medical treatment system according to a first embodiment of the invention.

FIG. 1 is a diagram schematically illustrating a medical treatment system 1 according to the first embodiment of the invention.

The medical treatment system 1 is used to perform a treatment (bonding or anastomosis) on a body tissue by applying energy to the body tissue as a treatment target. As illustrated in FIG. 1, the medical treatment system 1 comprises a medical treatment device 2, a control device 3, and a foot switch 4.

The medical treatment device 2 is, for example, a linear type surgical treatment tool which is used to perform a treatment for a body tissue through an abdominal wall. As illustrated in FIG. 1, the medical treatment device 2 comprises a handle 5, a shaft 6, and a grasper 7.

The handle 5 is gripped by an operator. As illustrated in FIG. 1, the handle 5 is provided with an operation knob, or lever 51.

As illustrated in FIG. 1, the shaft 6 has a substantially cylindrical shape and one end thereof is connected to the handle 5. Further, the grasper 7 is attached to the other end of the shaft 6. An opening/closing mechanism (not illustrated) which opens and closes jaws 8 and 8' (FIG. 1) constituting the grasper 7 in response to an operation of the operation knob 51 by the operator is provided inside the shaft 6. Further, an electric cable C (FIG. 1) which is connected to the control device 3 is disposed inside the shaft 6 from one end side to the other end side through the handle 5.

Figure 2:
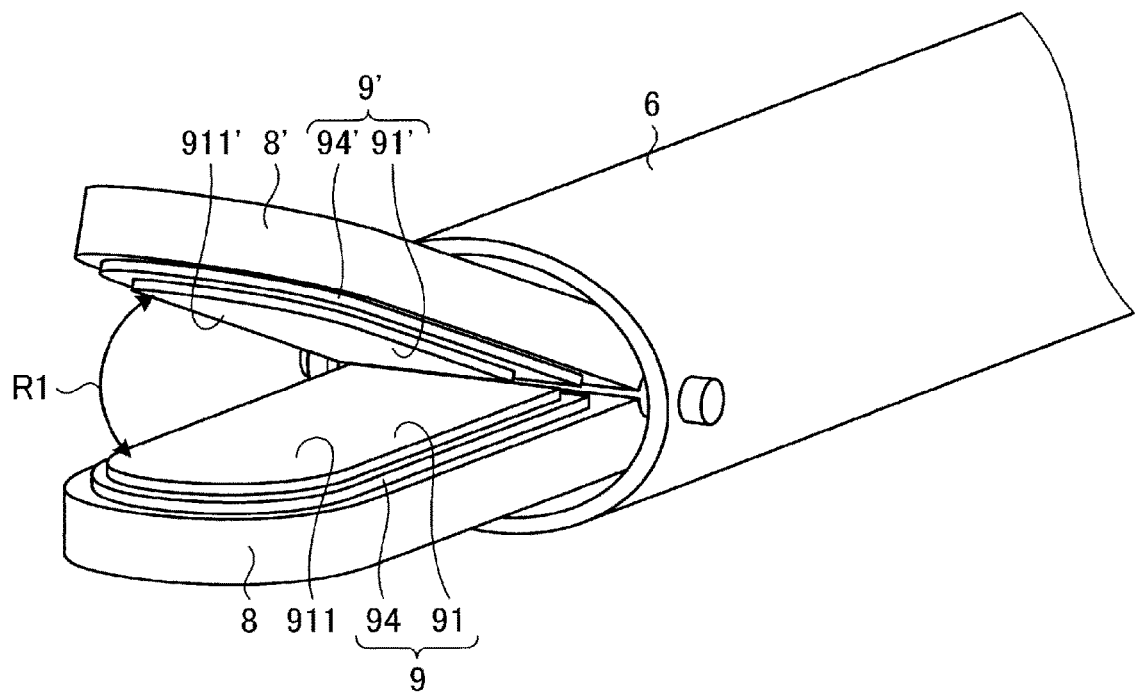
FIG. 2 is a diagram illustrating a front end part of the medical treatment device illustrated in FIG. 1.

FIG. 2 is an enlarged view of a front end part of the medical treatment device 2.

In FIGS. 1 and 2, an element without "'" and an element with "'" have the same configuration. The same also applies to the drawings below.

The grasper 7 is a portion which grasps a body tissue and performs a treatment for the body tissue. As illustrated in FIG. 1 or 2, the grasper 7 comprises the pair of jaws 8 and 8'.

The pair of jaws 8 and 8' is axially supported by the other end of the shaft 6 to be opened and closed in a direction indicated by an arrow R1 (FIG. 2) and grasps a body tissue in response to an operation of the operation knob 51 by the operator.

As illustrated in FIG. 2, the pair of jaws 8 and 8' is respectively provided with treatment energy application structures 9 and 9'.

Since the treatment energy application structures 9 and 9' have the same configuration, hereinafter, only the treatment energy application structure 9 will be described.

Figure 3:
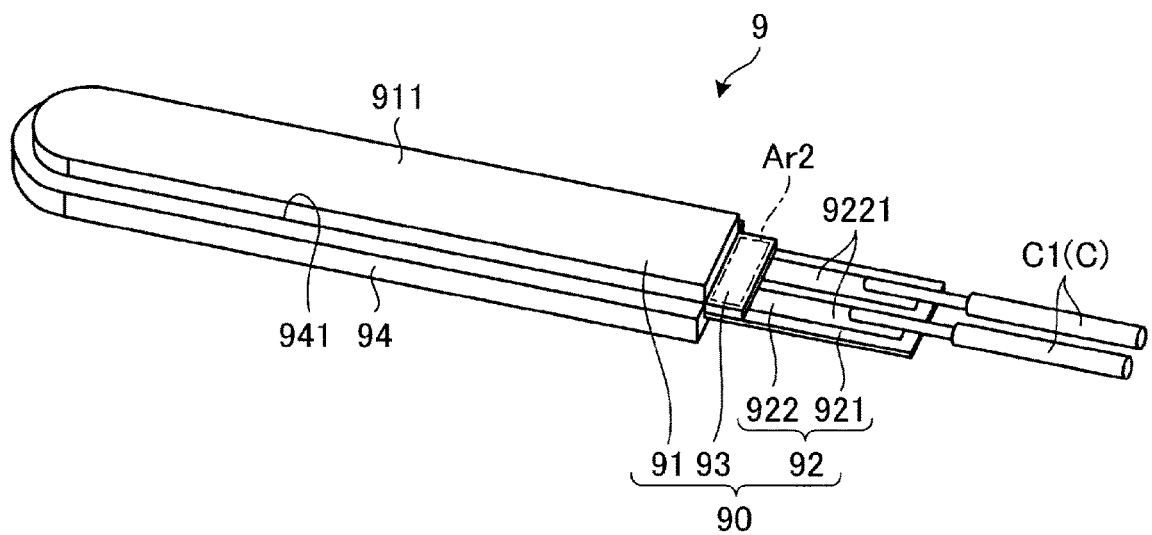
FIG. 3 is a diagram illustrating a treatment energy application structure illustrated in FIG. 2.
Figure 4:
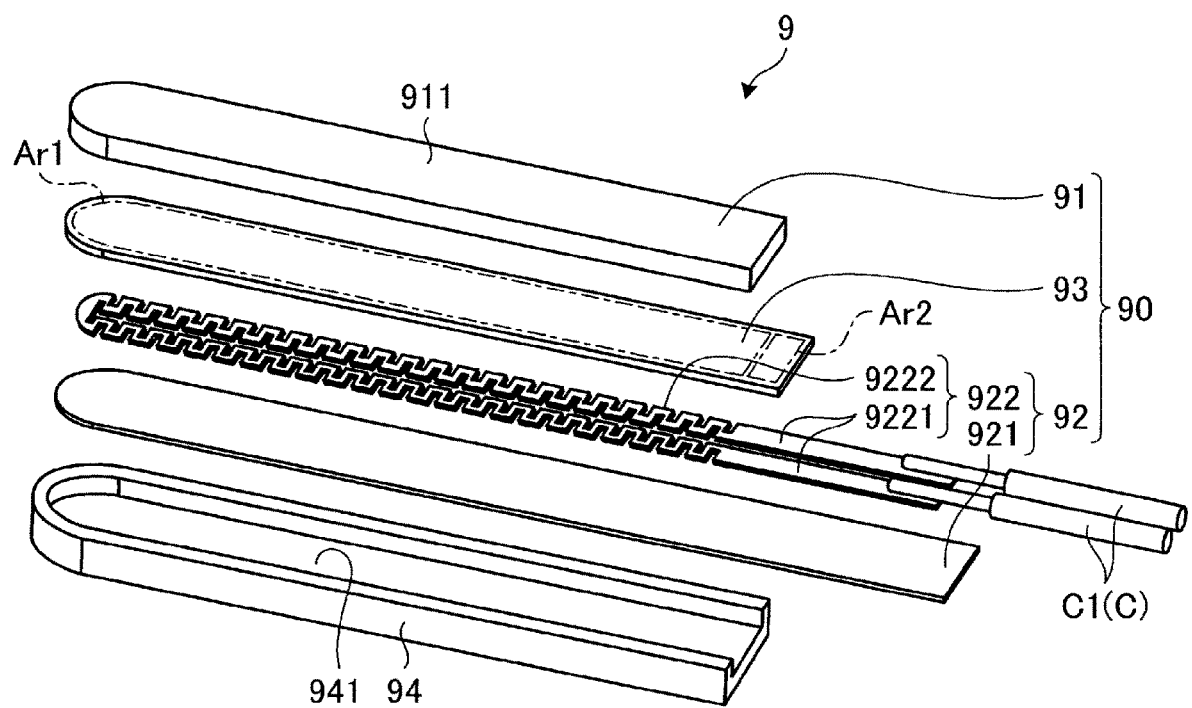
FIG. 4 is a diagram illustrating the treatment energy application structure illustrated in FIG. 2.

FIGS. 3 and 4 are diagrams illustrating the treatment energy application structure 9. Specifically, FIG. 3 is a perspective view illustrating the treatment energy application structure 9 when viewed from above in FIG. 2. FIG. 4 is an exploded perspective view of FIG. 3.

The treatment energy application structure 9 is attached to an upper surface of the jaw 8 disposed at the lower side in FIGS. 1 and 2. That is, the treatment energy application structure 9 is disposed between the jaw 8 and the jaw 8' in a direction of a grasping surface of grasping a body tissue. The treatment energy application structure 9 applies heat energy to the body tissue under the control of the control device 3. As illustrated in FIG. 3 or 4, the treatment energy application structure 9 comprises a heat transfer plate 91, a flexible substrate 92, an adhesive sheet 93, and a cover 94.

The heat transfer plate 91 is, for example, an elongated thin plate which is formed of copper or the like and in a state where the treatment energy application structure 9 is attached to the jaw 8, a treatment surface 911 which is one plate surface is directed toward the jaw 8' (in FIGS. 1 and 2, upward). The heat transfer plate 91 transfers heat of the flexible substrate 92 to a body tissue (i.e., applies heat energy to the body tissue) by bringing the treatment surface 911 into contact with the body tissue while the body tissue is grasped by the jaws 8 and 8'.

The flexible substrate 92 serves as a sheet heater which generates heat from a part thereof and heats the heat transfer plate 91 by the heat. As illustrated in FIG. 3 or 4, the flexible substrate 92 comprises a substrate 921 and a heating pattern 922.

The substrate 921 is an elongated sheet which is formed of an insulation material such as polyimide.

Here, a width of the substrate 921 is set to be substantially the same as a width of the heat transfer plate 91. Further, a length (in FIG. 4, a length in the horizontal direction) of the substrate 921 is set to be longer than a length (in FIG. 4, a length in the horizontal direction) of the heat transfer plate 91.

The heating pattern 922 is used to heat the heat transfer plate 91, the heating pattern 922 is formed by adhering on one surface of the substrate 921 or by processing a metal film formed with evaporation. As illustrated in FIG. 3 or 4, the heating pattern 922 comprises a pair of lead wire connection portions 9221 and an electric resistance pattern 9222 (FIG. 4).

Here, a material of the heating pattern 922 is stainless steel or platinum.

The pair of lead wire connection portions 9221 extends from one end side (in FIG. 4, a right end side) of the substrate 921 toward the other end side (in FIG. 4, a left end side), and faces each other in the width direction of the substrate 921. Two lead wires C1 (FIG. 4) constituting the electric cable C are respectively bonded (connected) to the pair of lead wire connection portions 9221.

One end of the electric resistance pattern 9222 is connected (electrically connected) to one lead wire connection portion 9221, a U-shape is formed, for example, from the one end to follow an outer edge shape of the substrate 921, and the other end thereof is connected (electrically connected) to the other lead wire connection portion 9221. The electric resistance pattern 9222 generates heat when a voltage is applied (supplied) to the pair of lead wire connection portions 9221 through two lead wires C1 by the control device 3.

The adhesive sheet 93 is interposed between the heat transfer plate 91 and the flexible substrate 92 (FIGS. 3 and 4) to allow the heat transfer plate 91 and the flexible substrate 92 to adhere to each other. The adhesive sheet 93 is an elongated sheet which has good thermal conductivity and electrical insulation properties and has high-temperature resistance and adhesiveness and is formed by mixing ceramic having high thermal conductivity such as, for example, alumina or aluminum nitride with epoxy resin.

Here, a width of the adhesive sheet 93 is set to be substantially the same as widths of the heat transfer plate 91 and the substrate 921. Further, a length (in FIG. 4, a length in the horizontal direction) of the adhesive sheet 93 is set to be longer than a length (in FIG. 4, a length in the horizontal direction) of the heat transfer plate 91 and is set to be shorter than a length (in FIG. 4, a length in the horizontal direction) of the substrate 921. The adhesive sheet 93 comprises two areas, that is, a first area Ar1 (FIG. 4) to cover the entirety of the heat transfer plate 91, the entirety of the electric resistance pattern 922, and a part of the pair of lead wire connection portions 9221 when viewed from the longitudinal direction of the adhesive sheet 93 while the adhesive sheet is interposed between the heat transfer plate 91 and the flexible substrate 92, and a second area Ar2 (FIGS. 3 and 4) which protrudes from the heat transfer plate 91 toward a right side in FIG. 4 to cover a part of the pair of lead wire connection portions 9221. The first area Ar1 may cover at least the entire surface of the electric resistance pattern 922.

The heat transfer plate 91, the adhesive sheet 93, and the flexible substrate 92 constitute a heat transfer unit 90 (FIGS. 3 and 4) as will be described below.

The cover 94 is formed of an insulation resin, supports the heat transfer unit 90 (FIG. 3), and is attached to the jaw 8. As illustrated in FIG. 3 or 4, the cover 94 is formed as an elongated plate body having a concave portion 941 formed in one surface (in FIG. 4, an upper plate surface).

The concave portion 941 has substantially the same plane shape as the plane shape of the heat transfer plate 91. Further, in a side wall portion constituting the concave portion 941, there is an opening in a right side wall portion in FIG. 4. For this reason, as illustrated in FIG. 3, the heat transfer unit 90 is attached into the concave portion 941 while a part of the flexible substrate 92 and the second area Ar2 of the adhesive sheet 93 protrude outward.

In the treatment energy application structure 9, the other plate surface (the plate surface without the concave portion 941) of the cover 94 is attached to the jaw 8 (FIG. 2).

(Heat Transfer Unit Assembling Method)

In the first embodiment, the adhesive sheet 93 is formed as an adhesive sheet which affects an adhesion function by a pressure applied thereto. As the adhesive sheet 93, an adhesive sheet which exhibits an adhesion function by at least one of a pressure and heat applied thereto may be employed.

Hereinafter, a method for assembling the heat transfer unit 90 in a case where the adhesive sheet 93 affecting an adhesion function by a pressure applied thereto is used will be described.

Figure 5:
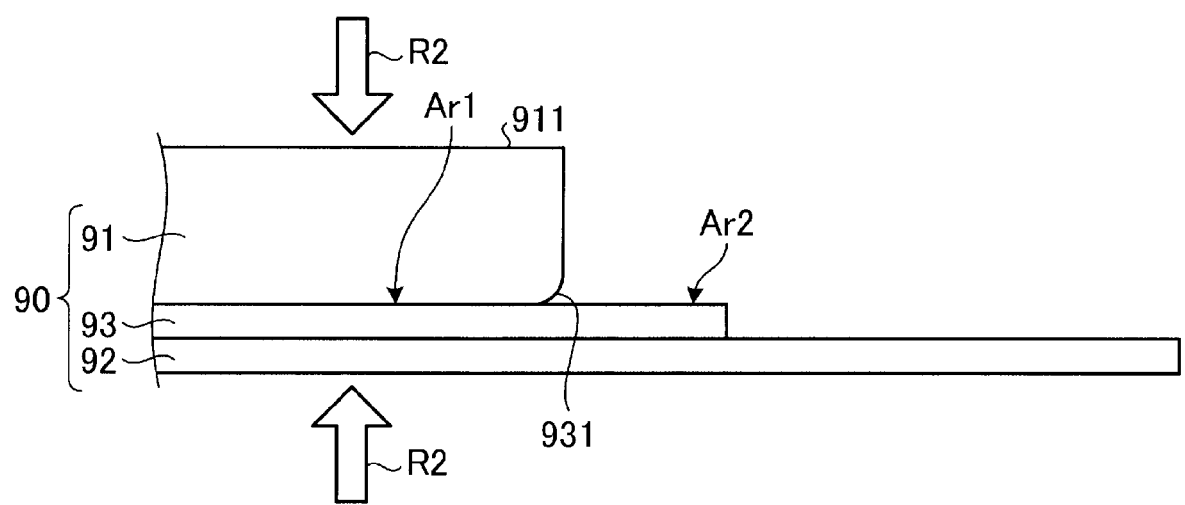
FIG. 5 is a diagram illustrating a method for assembling a heat transfer unit illustrated in FIGS. 3 and 4.

FIG. 5 is a diagram illustrating a method for assembling the heat transfer unit 90. Specifically, FIG. 5 is a diagram in which the heat transfer unit 90 is viewed from a lateral side.

First, as illustrated in FIG. 5, the adhesive sheet 93 is interposed between the heat transfer plate 91 and the flexible substrate 92 while the heat transfer plate 91, the flexible substrate 92, and the adhesive sheet 93 are positioned.

Next, a pressure is applied to the heat transfer plate 91 and the flexible substrate 92 in a direction indicated by an arrow R2 of FIG. 5 to pressurize the adhesive sheet 93.

By the above-described process, the first area Ar1 of the adhesive sheet 93 affects an adhesion function by a pressure applied from the heat transfer plate 91 and the flexible substrate 92 to allow the heat transfer plate 91 and the flexible substrate 92 to adhere to each other. Meanwhile, the second area Ar2 of the adhesive sheet 93 does not affect an adhesion function since a pressure is not applied from the heat transfer plate 91 and the flexible substrate 92 and thus does not adhere to any one of the heat transfer plate 91 and the flexible substrate 92.

In the configuration of the first embodiment, the second area Ar2 does not easily adhere to the flexible substrate 92. This is because the adhesive sheet 93 has an adhesion property on the front and rear surfaces thereof due to its feature and the adhesive sheet 93 needs to be interposed between the other members in order to adhere to the other members by the pressurization. That is, when a tool is used to fix the second area Ar2, the tool itself adheres to the adhesive sheet.

Meanwhile, it is difficult to remove the second area Ar2 of the adhesive sheet 93, that is, it is difficult to form the adhesive sheet to match the length of the heat transfer plate 91 in consideration of safety. In other words, when the flexible substrate 92 including the electric resistance pattern 922 is inclined with respect to the heat transfer plate 91 to contact the heat transfer plate 91 during the treatment, electric power is supplied to the heat transfer plate 91. In order to avoid this situation, there is a need to extend the adhesive sheet 93 having an insulation function to be longer than the heat transfer plate 91.

From the description above, the second area Ar2 of the adhesive sheet 93 does not adhere to any one of the heat transfer plate 91 and the flexible substrate 92.

In the above-described assembling method, when a pressure is applied in a direction indicated by the arrow R2 of FIG. 5 while the heat transfer plate 91 has an edge, a pressure is intensively applied from the edge portion to a boundary portion between the first area Ar1 and the second area Ar2 of the adhesive sheet 93 and thus a load is applied to the adhesive sheet 93.

Here, in the first embodiment, as illustrated in FIG. 5, a corner 931 facing the adhesive sheet 93 in the heat transfer plate 91 is subjected to a chamfer. The chamfer is defined as at least a bevel or fillet.

The foot switch 4 is operated by a foot of the operator. The medical treatment device 2 (the electric resistance pattern 9222) is turned on and off by the control device 3 in response to the operation of the foot switch 4.

Means for switching between on and off states is not limited to the foot switch 4 and may be a switch which is operated by a hand.

The control device 3 comprises a CPU (Central Processing Unit) and the like and generally controls an operation of the medical treatment device 2 in accordance with a predetermined control program. More specifically, the control device 3 heats the heat transfer plate 91 by applying a voltage to the electric resistance pattern 9222 through the electric cable C in response to an operation (a power on/off operation) of the foot switch 4 by the operator.

Next, an operation (an operation method) of the medical treatment system 1 will be described.

The operator grips the medical treatment device 2 and inserts a front end part (a part of the grasper 7 and the shaft 6) of the medical treatment device 2 into, for example, an abdominal cavity through an abdominal wall by the use of a trocar. Then, the operator operates the operation knob 51 to pinch a body tissue of a treatment target by the jaws 8 and 8'.

Next, the operator operates the foot switch 4 to select a power on state in which power is supplied from the control device 3 to the medical treatment device 2. When the power on state is selected, the control device 3 heats the heat transfer plate 91 by applying a voltage to the heating pattern 922 through the electric cable C. Then, the body tissue contacting the heat transfer plate 91 is treated by the heat of the heat transfer plate 91.

In the treatment energy application structure 9 according to the first embodiment, the corner 931 contacting the adhesive sheet 93 in the heat transfer plate 91 is chamfered.

For this reason, when the heat transfer unit 90 is assembled, a pressure is not intensively applied to a boundary portion between the first area Ar1 and the second area Ar2 of the adhesive sheet 93 even when a pressure is applied to the heat transfer plate 91 and the flexible substrate 92 in a direction indicated by the arrow R2 of FIG. 5 such that the flexible substrate 92 and the adhesive sheet 93 are inclined with respect to the heat transfer plate 91. Further, a pressure is not intensively applied to the boundary portion when the medical treatment device 2 is used, that is, even when a body tissue is grasped by the pair of jaws 8 and 8'.

Thus, a load on the adhesive sheet 93 can be reduced.

Further, in the first embodiment, the corner 931 of the heat transfer plate 91 is subjected to a chamfer. Particularly, the corner 931 may be subjected to a straight edge chamfer, such as a bevel or C-chamfer or the corner 931 may be subjected to a curved surface without any edge, such as a fillet or R-chamfer. R-chamfering may be more suitable to avoid a sharp edge. Meanwhile, in the case of the C-chamfer, there is a merit that a manufacturing cost is lower than that of the R-chamfer.

Figure 6A:
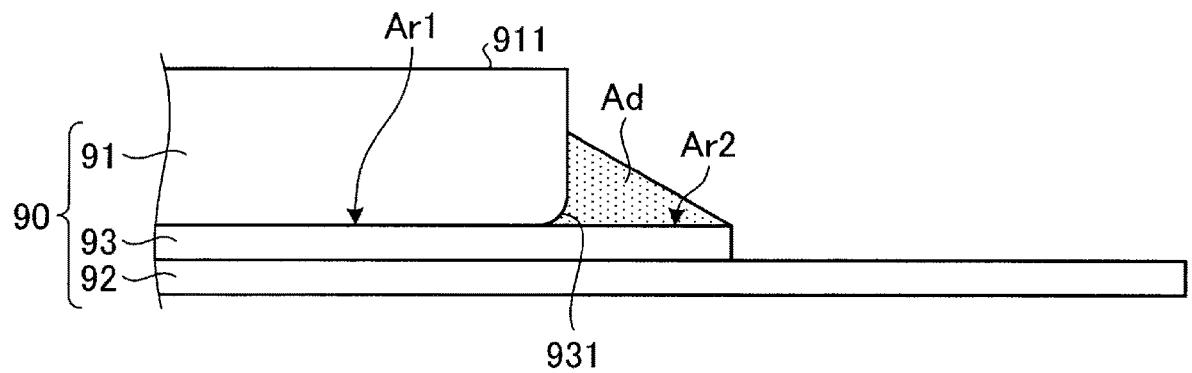
FIG. 6A is a diagram illustrating Modified Example of the first embodiment of the invention.
Figure 6B:
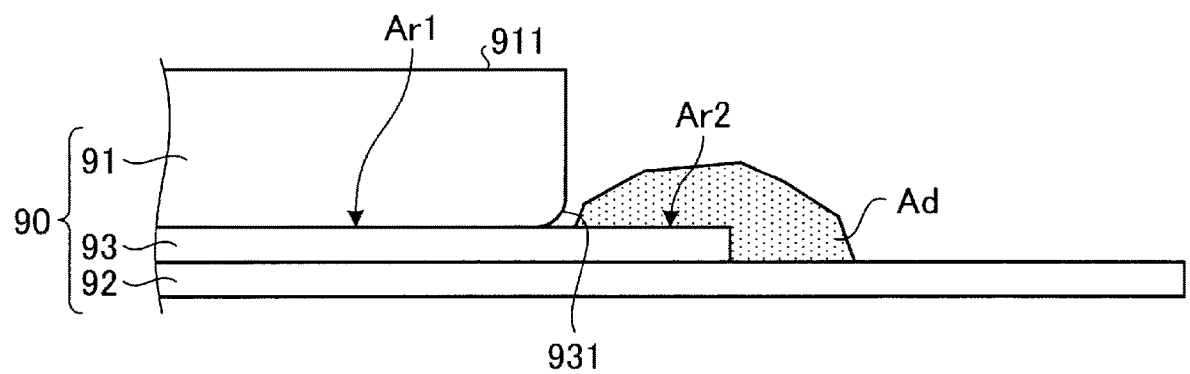
FIG. 6B is a diagram illustrating Modified Example of the first embodiment of the invention.
Figure 6C:
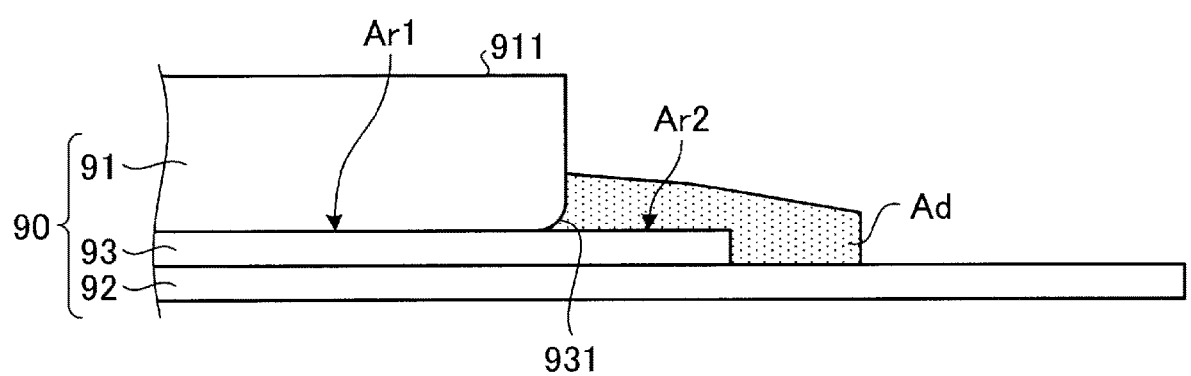
FIG. 6C is a diagram illustrating Modified Example of the first embodiment of the invention.

FIGS. 6A to 6C are diagrams illustrating Modified Example of the first embodiment of the invention. Specifically, FIGS. 6A to 6C are diagrams corresponding to FIG. 5.

In the first embodiment, a configuration may be employed in which the second area Ar2 of the adhesive sheet 93 adheres to at least any one of the heat transfer plate 91 and the flexible substrate 92 by an insulation adhesive Ad after the assembly of the heat transfer unit 90 as illustrated in FIGS. 6A to 6C.

Specifically, FIG. 6A illustrates a configuration in which the second area Ar2 and the heat transfer plate 91 adhere to each other by the adhesive Ad. FIG. 6B illustrates a configuration in which the second area Ar2 and the flexible substrate 92 adhere to each other by the adhesive Ad. FIG. 6C illustrates a configuration in which the second area Ar2 adheres to both the heat transfer plate 91 and the flexible substrate 92 by the adhesive Ad.

As described above, since the adhesive Ad is used, the second area Ar2 which does not work on an adhesion function and does not adhere to any one of the heat transfer plate 91 and the flexible substrate 92 can be fixed to at least one of the heat transfer plate 91 and the flexible substrate 92.

Next, a second embodiment of the invention will be described.

In the description below, the same reference signs are used to designate the same elements as those of the first embodiment, and a detailed explanation thereof will be omitted or simplified.

A medical treatment system according to the second embodiment is different from the medical treatment system 1 described in the first embodiment in that the configurations of the treatment energy application structures 9 and 9' are different. For this reason, hereinafter, a configuration of a treatment energy application structure according to the second embodiment will be described.

Figure 7:
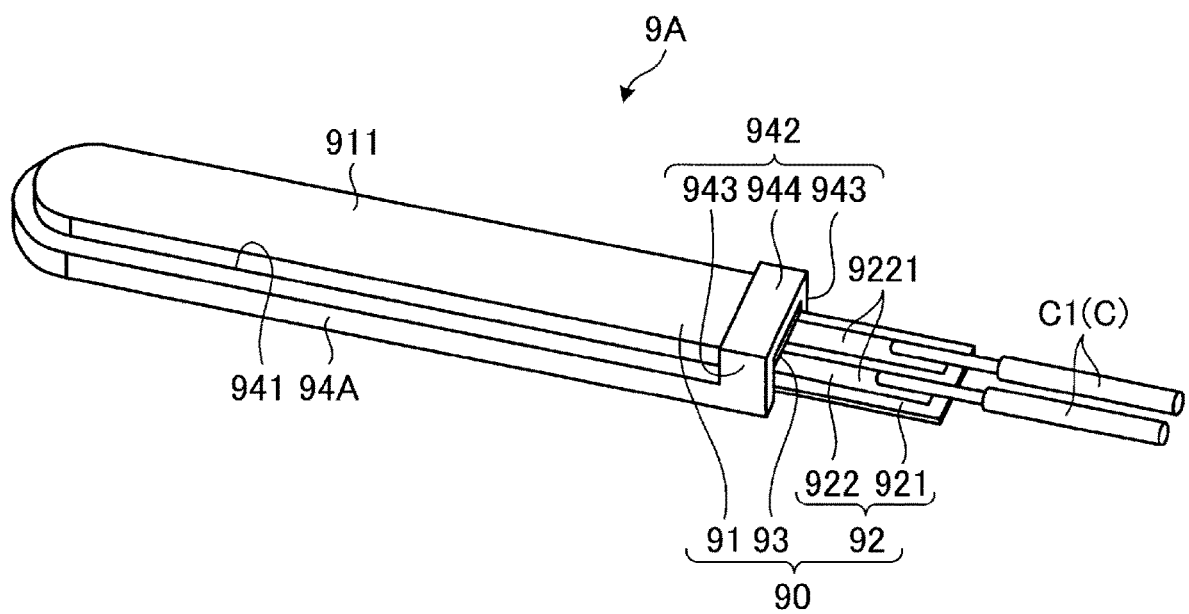
FIG. 7 is a diagram illustrating a treatment energy application structure according to a second embodiment of the invention.

FIG. 7 is a diagram illustrating a treatment energy application structure 9A according to the second embodiment of the invention. Specifically, FIG. 7 is a diagram corresponding to FIG. 3.

The treatment energy application structure 9A provided in the jaw 8 and a treatment energy application structure (not illustrated) provided in the jaw 8' have the same configuration. For this reason, hereinafter, only the treatment energy application structure 9A will be described.

As illustrated in FIG. 7, the treatment energy application structure 9A is different from the treatment energy application structure 9 described in the first embodiment in that the cover 94 is different.

Figure 8:
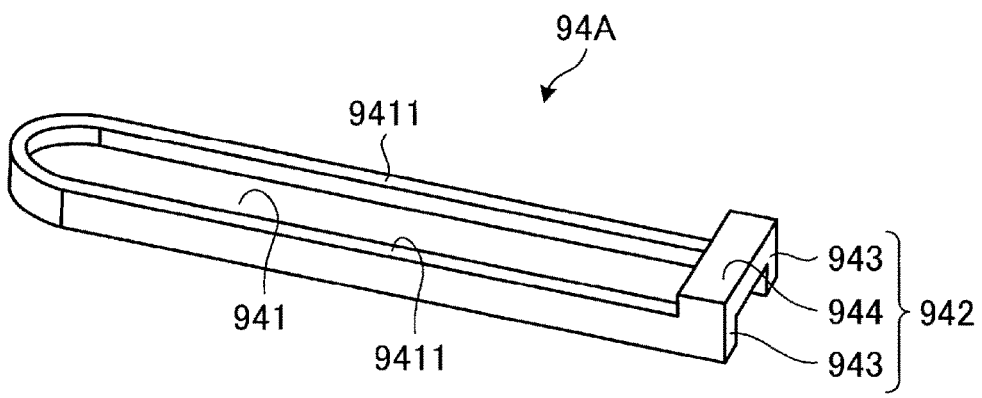
FIG. 8 is a diagram illustrating a cover illustrated in FIG. 7.

FIG. 8 is a diagram illustrating a cover 94A.

As illustrated in FIG. 7 or 8, the cover 94A according to the second embodiment is different from the cover 94 (FIGS. 3 and 4) described in the first embodiment in that a fixed portion 942 is provided.

As illustrated in FIG. 8, the fixed portion 942 of cover 94A comprises a pair of base portions 943 and a bridge portion 944.

The pair of base portions 943 is integrated with the right ends of the pair of side walls 9411 (FIG. 8) facing each other in the width direction of the cover 94A, among the side wall constituting the concave portion 941 in FIG. 8. A distance between the pair of base portions 943 is substantially equal to a distance between the pair of side walls 9411 (the width of the heat transfer plate 91).

The bridge portion 944 is provided at the upper ends of the pair of base portions 943 in FIG. 8.

Figure 9:
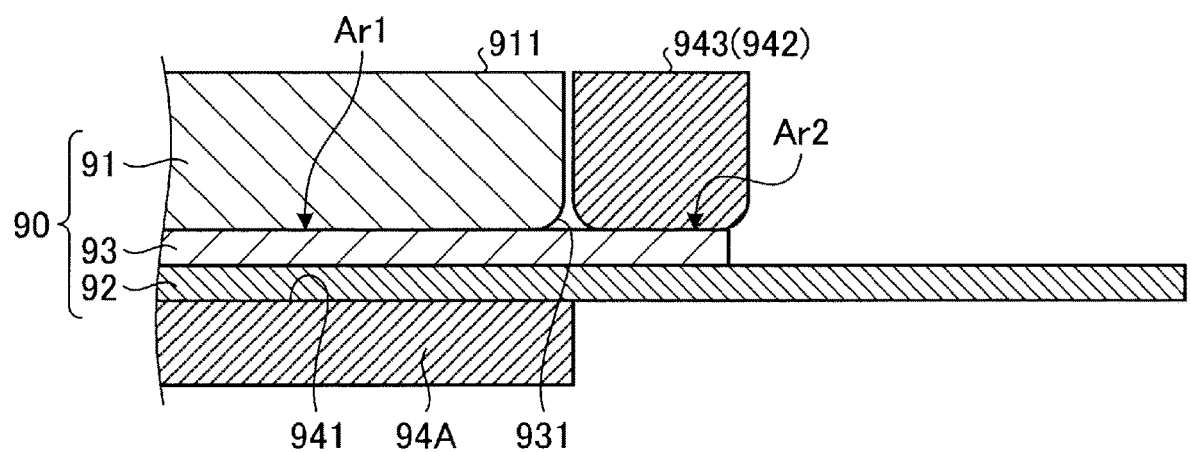
FIG. 9 is a diagram illustrating a function of a fixed portion illustrated in FIGS. 7 and 8.

FIG. 9 is a diagram illustrating a function of the fixed portion 942. Specifically, FIG. 9 is a cross-sectional view obtained by cutting the heat transfer unit 90 and the cover 94A along a plane passing through center positions of the heat transfer unit 90 and the cover 94A in the width direction.

In a state where the heat transfer unit 90 is attached into the concave portion 941, a part of the flexible substrate 92 protrudes outward while passing through a space surrounded by the pair of side walls 9411 and the bridge portion 944 as illustrated in FIG. 7. Further, the second area Ar2 of the adhesive sheet 93 is positioned to a space surrounded by the pair of side walls 9411 and the bridge portion 944 as illustrated in FIG. 9.

The fixed portion 942 (the bridge portion 944) has a function of applying a pressure to the flexible substrate 92 in the second area Ar2 while the heat transfer unit 90 is attached into the concave portion 941.

Here, as illustrated in FIG. 9, the bridge portion 944 has the corner 931 contacting the adhesive sheet 93, and the corner 931 is subjected to R-chamfering similarly to the heat transfer plate 91. The corner may be subjected to C-chamfering instead of the R-chamfering.

According to the second embodiment, a following effect is obtained other than the same effect as that of the first embodiment.

In the treatment energy application structure 9A according to the second embodiment, the fixed portion 942 of the cover 94A applies a pressure to the flexible substrate 92 in the second area Ar2.

For this reason, the second area Ar2 which does not exhibit an adhesion function and does not adhere to any one of the heat transfer plate 91 and the flexible substrate 92 can be set in a fixed state.

Modified Example of Second Embodiment

In the second embodiment, the fixed portion 942 has a function of applying a pressure to the flexible substrate 92 in the second area Ar2, but the invention is not limited thereto.

For example, the fixed portion 942 may not have the pressure application function and a rear surface (a surface facing the second area Ar2) of the bridge portion 944 may have an adhesion property to allow the bridge portion 944 to adhere to the second area Ar2.

Further, for example, the bridge portion 944 may adhere to the second area Ar2 while the fixed portion 942 has the pressure application function as described above.

Although embodiments of the invention have been described so far, the invention is not limited to the first and the second embodiments or Modified Examples thereof.

In the first and the second embodiments or Modified Examples thereof, the treatment energy application structures 9 (9A) and 9' are respectively provided at both jaws 8 and 8', but the invention is not limited thereto. For example, the treatment energy application structure may be provided only at any one of the jaws 8 and 8'.

In the first and the second embodiments or Modified Examples thereof, the treatment energy application structures 9 (9A) and 9' are configured to apply heat energy to a body tissue, but the invention is not limited thereto. For example, high-frequency energy or ultrasonic energy may be applied to the body tissue instead of the heat energy.

In the first and the second embodiments or Modified Examples thereof, the heat transfer plate 91 may have a configuration in which corner contacting the other portions of the adhesive sheet 93 are also chamfered in addition to the corner 931 contacting the boundary portion between the first area Ar1 and the second area Ar2 of the adhesive sheet 93.

In the first and the second embodiments or Modified Examples thereof, the shapes of the heat transfer plate 91, the flexible substrate 92, and the adhesive sheet 93 are not limited to the shapes described in the first and the second embodiments or Modified Examples thereof. For example, similarly to Patent Literature 1, a U-shape may be formed entirely in order to ensure a movement path of a cutter.

Figure 10:
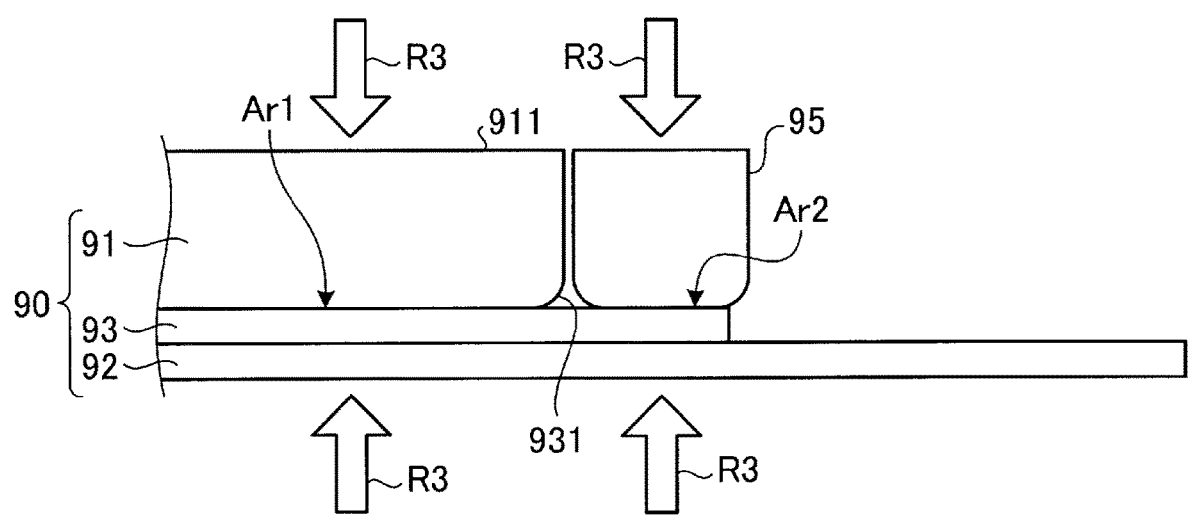
FIG. 10 is a diagram illustrating Modified Examples of the first and second embodiments of the invention.

FIG. 10 is a diagram illustrating Modified Examples of the first and the second embodiments of the invention. Specifically, FIG. 10 is a diagram corresponding to FIG. 5.

In the first and the second embodiments and Modified Examples thereof, a following assembling method may be employed as a method for assembling the heat transfer unit 90.

First, as illustrated in FIG. 10, similarly to the first and the second embodiments and Modified Examples thereof, the adhesive sheet 93 is interposed between the heat transfer plate 91 and the flexible substrate 92 while the heat transfer plate 91, the flexible substrate 92, and the adhesive sheet 93 are positioned. Then, as illustrated in FIG. 10, an insulation substrate 95 is put on the second area Ar2.

Here, the insulation substrate 95 is a plate body which is formed of insulation resin to have substantially the same plane shape as that of the second area Ar2 and to have substantially the same thickness as that of the heat transfer plate 91. Further, as illustrated in FIG. 10, a portion contacting the adhesive sheet 93 in the insulation substrate 95 is subjected to R-chamfering similarly to the heat transfer plate 91. The plane shape of the insulation substrate 95 is not limited to a plane shape which is substantially the same as that of the second area Ar2 and the other plane shapes may be used as long as the plane shapes cover the second area Ar2.

Next, the adhesive sheet 93 is pressurized by a pressure applied to the heat transfer plate 91, the insulation substrate 95, and the flexible substrate 92 in a direction indicated by an arrow R3 of FIG. 10.

By the above-described process, the first area Ar1 of the adhesive sheet 93 exhibits an adhesion function by a pressure applied from the heat transfer plate 91 and the flexible substrate 92 to allow the heat transfer plate 91 and the flexible substrate 92 to adhere to each other. Similarly, the second area Ar2 of the adhesive sheet 93 exhibits an adhesion function by a pressure applied from the insulation substrate 95 and the flexible substrate 92 to allow the insulation substrate 95 and the flexible substrate 92 to adhere to each other.

When a configuration using the insulation substrate 95 is employed, the same effects as those of Modified Example (FIG. 6A to FIG. 6C) of the first embodiment, the second embodiment (FIG. 7 to FIG. 9), and Modified Example thereof are obtained in addition to the effect of the first embodiment.

If the above-described assembling method is employed, the corner of the heat transfer plate 91 or the insulation substrate 95 does not need to be essentially chamfered.

The invention claimed is:

1. A treatment energy application structure comprising:
a flexible substrate having, on one surface thereof, an electric resistance pattern and a lead wire connection portion, the electric resistance pattern being configured to generate heat by power supply, and the lead wire connection portion being configured to be electrically connected to the electric resistance pattern and connected to a lead wire;
a heat transfer plate facing the one surface of the flexible substrate and configured to transfer the heat from the electric resistance pattern to a body tissue; and
an insulating adhesive sheet interposed between the flexible substrate and the heat transfer plate to allow the flexible substrate and the heat transfer plate to adhere to each other,
wherein the insulating adhesive sheet comprises:
a first area to cover at least an entire surface of the electric resistance pattern and the heat transfer plate; and
a second area protruding from the heat transfer plate to cover a part of the lead wire connection portion and wherein the second area adheres to at least one of the heat transfer plate and the flexible substrate by an adhesive, and
wherein the heat transfer plate has a corner facing the insulating adhesive sheet, and the corner is subject to a chamfer.

2. The treatment energy application structure according to claim 1,
wherein the chamfer of the corner is a fillet.

3. The treatment energy application structure according to claim 1,
further comprising a cover for supporting the heat transfer plate and the flexible substrate adhering to each other through the insulating adhesive sheet while a treatment surface of the heat transfer plate is exposed outside;
wherein the cover comprises a fixed portion facing the flexible substrate through the second area, and
wherein the fixed portion is configured to apply a pressure to the second area toward the flexible substrate.

4. The treatment energy application structure according to claim 3, wherein the fixed portion adheres to the second area.

5. A medical treatment device comprising:
a handle configured to be in electrical communication with a controller;
an elongated shaft configured to be attached to the handle via one end thereof;
a grasper defined by a pair of jaws configured to be attached to an opposed end of the shaft and being capable of gripping a treatment target; and
a treatment energy application structure configured to be disposed within the grasper, wherein the treatment energy application structure
having a flexible substrate, the flexible substrate includes, on one surface thereof, an electric resistance pattern and a lead wire connection portion, the electric resistance pattern being configured to generate heat by power supply, and the lead wire connection portion being configured to be electrically connected to the electric resistance pattern and connected to a lead wire;
a heat transfer plate facing the one surface of the flexible substrate and configured to transfer the heat from the electric resistance pattern to a body tissue;
an insulating adhesive sheet interposed between the flexible substrate and the heat transfer plate to allow the flexible substrate and the heat transfer plate to adhere to each other, wherein the insulating adhesive sheet comprises
a first area to cover at least an entire surface of the electric resistance pattern and the heat transfer plate, and
a second area protruding from the heat transfer plate to cover a part of the lead wire connection portion,
wherein the heat transfer plate has a corner facing the insulating adhesive sheet, and the corner is subject to a chamfer, and
a cover for supporting the heat transfer plate and the flexible substrate adhering to each other through the insulating adhesive sheet while a treatment surface of the heat transfer plate is exposed outside;
wherein the cover comprises a fixed portion facing the flexible substrate through the second area, and
wherein the fixed portion is configured to apply a pressure to the second area toward the flexible substrate.

6. A treatment energy application structure comprising:
a substrate having, on one surface thereof, an electric resistance pattern and a lead wire connection portion, the electric resistance pattern being configured to generate heat by power supply, and the lead wire connection portion being configured to be electrically connected to the electric resistance pattern and connected to a lead wire;
a heat transfer plate facing the one surface of the substrate;
an insulating adhesive sheet interposed between the substrate and the heat transfer plate to adhere to each other,
wherein the insulating adhesive sheet comprises:
a first area to cover the entirety of the heat transfer plate; and
a second area protruding from the heat transfer plate to cover a part less than the entirety of the lead wire connection portion; and
an adhesive, the adhesive adhering the second area to at least one of the heat transfer plate and the substrate.

7. The treatment energy application structure of claim 6, wherein the adhesive adheres the second area to the heat transfer plate and the substrate.

8. The treatment energy application structure of claim 6, wherein the heat transfer plate has a corner facing the insulating adhesive sheet, and the corner is subject to a chamfer.

9. The treatment energy application structure of claim 6, wherein the substrate is a flexible substrate.

10. A treatment energy application structure comprising:
a substrate having, on one surface thereof, an electric resistance pattern and a lead wire connection portion, the electric resistance pattern being configured to generate heat by power supply, and the lead wire connection portion being configured to be electrically connected to the electric resistance pattern and connected to a lead wire;
a heat transfer plate facing the one surface of the substrate;
a cover comprising a bridge portion facing the one surface of the substrate;
an insulating adhesive sheet interposed between the substrate and both the heat transfer plate and the bridge portion to allow the substrate to adhere to both the heat transfer plate and the bridge portion, wherein the insulating adhesive sheet comprises:
  a first area to cover the entirety of the heat transfer plate; and
  a second area protruding from the heat transfer plate to cover a part of the lead wire connection portion;
wherein the bridge portion faces the substrate through the second area.

11. The treatment energy application structure of claim 10, wherein the heat transfer plate is formed of a conducting material and wherein the bridge portion is formed of an insulation resin.

12. The treatment energy application structure of claim 10, wherein the substrate is a flexible substrate.

* * * * *